(12) United States Patent
Bar-Tal et al.

(10) Patent No.: US 9,265,574 B2
(45) Date of Patent: Feb. 23, 2016

(54) MONITORING TISSUE TEMPERATURE WHILE USING AN IRRIGATED CATHETER

(75) Inventors: Meir Bar-Tal, Haifa (IL); Abraham Berger, Ramat-Gan (IL); Avri Hazan, Givataim (IL); Daniel Osadchy, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 1227 days.

(21) Appl. No.: 13/113,159

(22) Filed: May 23, 2011

(65) Prior Publication Data

US 2011/0224573 A1    Sep. 15, 2011

Related U.S. Application Data

(63) Continuation-in-part of application No. 13/036,469, filed on Feb. 28, 2011.

(60) Provisional application No. 61/312,447, filed on Mar. 10, 2010.

(51) Int. Cl.
*A61B 18/14* (2006.01)
*A61B 5/01* (2006.01)
*A61B 17/00* (2006.01)
*A61B 19/00* (2006.01)

(52) U.S. Cl.
CPC .............. *A61B 18/1492* (2013.01); *A61B 5/01* (2013.01); *A61B 2017/00084* (2013.01); *A61B 2019/461* (2013.01); *A61B 2019/467* (2013.01); *A61B 2019/502* (2013.01); *A61B 2019/504* (2013.01); *A61B 2019/5251* (2013.01)

(58) Field of Classification Search
CPC ............... A61B 18/1492; A61B 2019/461; A61B 2019/467; A61B 2019/502; A61B 2019/504; A61B 2017/00084; A61B 5/01
USPC ............... 606/41, 45–50; 607/101, 102, 122
See application file for complete search history.

(56) References Cited

U.S. PATENT DOCUMENTS

| 5,423,808 | A  | * | 6/1995  | Edwards et al. ........... 606/34  |
| 5,500,012 | A  | * | 3/1996  | Brucker et al. ........... 607/122 |
| 5,672,173 | A  | * | 9/1997  | Gough et al. ........... 606/41    |
| 5,688,267 | A  | * | 11/1997 | Panescu et al. ........... 606/41  |
| 6,134,463 | A  | * | 10/2000 | Wittkampf et al. ........... 600/374 |
| 6,524,308 | B1 |   | 2/2003  | Muller                             |
| 7,160,296 | B2 | * | 1/2007  | Pearson et al. ........... 606/42  |
| 2007/0049915 | A1 | | 3/2007  | Haemmerich                         |
| 2008/0161797 | A1 | | 7/2008  | Wang                               |

(Continued)

FOREIGN PATENT DOCUMENTS

EP    2364664 A1    9/2011
JP    1994315541 A  11/2014

(Continued)

OTHER PUBLICATIONS

European Search Report Appln No. 12 16 9100 dated Aug. 21, 2012.
Japanese Notice of Refusal mailed Jul. 7, 2015 for the corresponding Japanese Patent Application.

(Continued)

*Primary Examiner* — Michael Peffley

(57) ABSTRACT

Apparatus, consisting of a probe, configured to be inserted into a body cavity, and an electrode having an outer surface and an inner surface connected to the probe. The apparatus also includes a temperature sensor, protruding from the outer surface of the electrode, which is configured to measure a temperature of the body cavity.

28 Claims, 11 Drawing Sheets

(56) References Cited

U.S. PATENT DOCUMENTS

2010/0016848 A1 1/2010 Desai
2010/0079158 A1 4/2010 Bar-Tal et al.
2011/0224573 A1 9/2011 Bar-Tal

FOREIGN PATENT DOCUMENTS

| JP | 2015014038 A | 1/2015 |
| WO | WO 2008/039188 A1 | 4/2008 |
| WO | WO 2009/065140 A1 | 5/2009 |

* cited by examiner

MONITORING TISSUE TEMPERATURE WHILE USING AN IRRIGATED CATHETER

CROSS-REFERENCE TO RELATED APPLICATION

This application is a continuation-in-part of U.S. patent application Ser. No. 13/036,469, filed Feb. 28, 2011, which claims the benefit of priority of U.S. Provisional Application No. 61/312,447, filed Mar. 10, 2010, each of which is incorporated herein by reference in its entirety.

FIELD OF THE INVENTION

The present invention relates generally to ablation of body tissue, and specifically to measuring the temperature of the tissue during the ablation.

BACKGROUND OF THE INVENTION

Medical procedures involving ablation of the heart may be used to cure a variety of cardiac arrhythmia, as well as to manage atrial fibrillation. Such procedures are known in the art. Other medical procedures using ablation of body tissue, such as treating varicose veins, are also known in the art. The ablation energy for these procedures may be in the form of radio-frequency (RF) energy.

The application of the ablation energy to body tissue, if uncontrolled, may lead to an unwanted increase of temperature of the tissue. It is consequently important to measure the temperature of the tissue during any medical procedure involving ablation.

PCT application WO 2008/039,188, to Mon, filed 27 Sep. 2006, which is incorporated herein by reference, describes a probe having multiple temperature sensors along the probe.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

modeling physical parameters representative of a probe in proximity to body tissue during an ablation procedure performed by the probe;

measuring a subgroup of the physical parameters during a non-ablation stage of the ablation procedure so as to generate measured non-ablative values of the subgroup;

measuring the subgroup of the physical parameters during an ablation stage of the ablation procedure so as to generate measured ablative values of the subgroup;

in response to the modeling:

generating calculated non-ablative values of the subgroup for the non-ablation stage; and generating calculated ablative values of the subgroup for the ablation stage; and comparing the measured non-ablative values with the calculated non-ablative values, and comparing the measured ablative values with the calculated ablative values, so as to generate optimal values of the physical parameters.

Typically, the physical parameters include a matrix of temperatures of the body tissue.

In a disclosed embodiment the subgroup includes a temperature, and the measured non-ablative values include a first time constant of a first change of the temperature, and the measured ablative values include a second time constant of a second change of the temperature.

In another disclosed embodiment the method includes irrigating the tissue via the probe, wherein the subgroup includes an irrigation rate alternating between a first measured irrigation rate during the non-ablation stage and a second measured irrigation rate during the ablation stage.

In yet another disclosed embodiment, the subgroup includes power supplied by the probe, alternating between a first power level able to ablate the tissue during the ablation stage, and a second power level not able to ablate the tissue during the non-ablation stage.

Typically, the subgroup includes at least one of a location, an orientation, and a contact area of the probe with respect to the body tissue.

Typically, the ablation procedure consists of radio-frequency ablation of the body tissue.

There is further provided, according to an alternative embodiment of the invention, a method, including:

computing a first estimated geometrical vector representative of a location, an orientation, and a contact area of a probe with respect to body tissue in response to electrical impedances between the probe and the body tissue;

computing a second estimated geometrical vector of the probe in response to a set of thermal parameters associated with an ablation procedure performed on the tissue by the probe;

comparing the first and second estimated geometrical vectors to formulate an optimal geometric vector; and estimating a temperature of the tissue using the optimal geometric vector.

Typically, the probe includes two or more electrodes insulated from each other, and the electrical impedances are respectively measured between the two or more electrodes and the body tissue.

The first estimated geometrical vector may include a first distance, a first angle, and a first contact area between the probe and the body tissue, the second estimated geometrical vector may include a second distance, a second angle, and a second contact area between the probe and the body tissue, and the optimal geometrical vector may include a third distance, a third angle, and a third contact area between the probe and the body tissue.

In a disclosed embodiment the ablation procedure includes supplying ablation power intermittently to the tissue via the probe, so that the ablation power alternates between a first measured ablation power level sufficient for ablation of the tissue during an ablation stage, and a second measured ablation power level not sufficient for ablation of the tissue during a non-ablation stage.

Typically, computing the second estimated geometrical vector further includes computing the vector in response to the electrical impedances.

Estimating the temperature of the tissue may include estimating a map of temperature values for the tissue.

There is further provided, according to an embodiment of the present invention, apparatus, including:

a probe, configured to be placed in proximity to body tissue; and a controller which is configured to:

compute a first estimated geometrical vector representative of an orientation, and a contact area of the probe with respect to the body tissue in response to electrical impedances between the probe and the body tissue, compute a second estimated geometrical vector of the probe in response to a set of thermal parameters associated with an ablation procedure performed on the tissue by the probe, compare the first and second estimated geometrical vectors to formulate an optimal geometric vector, and estimate a temperature of the tissue using the optimal geometric vector.

There is further provided, according to an alternative embodiment of the present invention, apparatus, including:

a probe, configured to be placed in proximity to body tissue; and a controller which is configured to:

model physical parameters representative of the probe during an ablation procedure performed by the probe on the body tissue;

measure a subgroup of the physical parameters during a non-ablation stage of the ablation procedure so as to generate measured non-ablative values of the subgroup;

measure the subgroup of the physical parameters during an ablation stage of the ablation procedure so as to generate measured ablative values of the subgroup;

in response to the modeling:

generate calculated non-ablative values of the subgroup for the non-ablation stage; and generate calculated ablative values of the subgroup for the ablation stage; and compare the measured non-ablative values with the calculated non-ablative values, and compare the measured ablative values with the calculated ablative values, so as generate optimal values of the physical parameters.

There is further provided, according to an embodiment of the present invention, a computer software product consisting of a non-transitory computer-readable medium having computer program instructions recorded therein, which instructions, when read by a computer, cause the computer to:

model physical parameters representative of a probe in proximity to body tissue during an ablation procedure performed by the probe;

measure a subgroup of the physical parameters during a non-ablation stage of the ablation procedure so as to generate measured non-ablative values of the subgroup;

measure the subgroup of the physical parameters during an ablation stage of the ablation procedure so as to generate measured ablative values of the subgroup;

in response to the modeling:

generate calculated non-ablative values of the subgroup for the non-ablation stage; and generate calculated ablative values of the subgroup for the ablation stage; and compare the measured non-ablative values with the calculated non-ablative values, and compare the measured ablative values with the calculated ablative values, so as to generate optimal values of the physical parameters.

There is further provided, according to an embodiment of the present invention, apparatus, including:

a probe, configured to be inserted into a body cavity;

an electrode having an outer surface and an inner surface connected to the probe; and a temperature sensor, protruding from the outer surface of the electrode, configured to measure a temperature of the body cavity.

Typically, the temperature sensor protrudes from the outer surface of the electrode by no more than 0.7 mm.

In a disclosed embodiment the electrode includes a curved surface in the shape of a partial toroid, and the temperature sensor protrudes from the curved surface.

Typically, the apparatus includes at least one further temperature sensor protruding from the outer surface of the electrode and configured to measure a further temperature of the body cavity.

In another disclosed embodiment the apparatus includes an insulator which connects the temperature sensor to the outer surface.

In an alternative embodiment the apparatus includes a further electrode positioned on an exterior surface of the temperature sensor, wherein the exterior surface insulates the further electrode from the electrode. Contact between a distal tip of the probe and tissue of the body cavity may be determined in response to an impedance of the further electrode. A distance between a distal tip of the probe and tissue of the body cavity may be measured in response to an impedance of the further electrode. An angle between a distal tip of the probe and tissue of the body cavity may be measured in response to an impedance of the further electrode.

A depth of penetration of a distal tip of the probe into the tissue may be determined in response to an impedance of the further electrode. At least one of a location and an orientation of a distal tip of the probe may be determined in response to an impedance of the further electrode. A temperature map of tissue of the body cavity may be determined in response to an impedance of the further electrode.

In a further alternative embodiment the electrode includes a first electrode, the apparatus further including a second electrode protruding from the outer surface of the first electrode and insulated from the first electrode.

There is further provided, according to an embodiment of the present invention, a method, including:

configuring a probe to be inserted into a body cavity;

connecting an electrode having an outer surface and an inner surface to the probe; and configuring a temperature sensor to protrude from the outer surface of the electrode and to measure a temperature of the body cavity.

The present disclosure will be more fully understood from the following detailed description of the embodiments thereof, taken together with the drawings, in which:

DETAILED DESCRIPTION OF EMBODIMENTS

Overview

Figure 1:
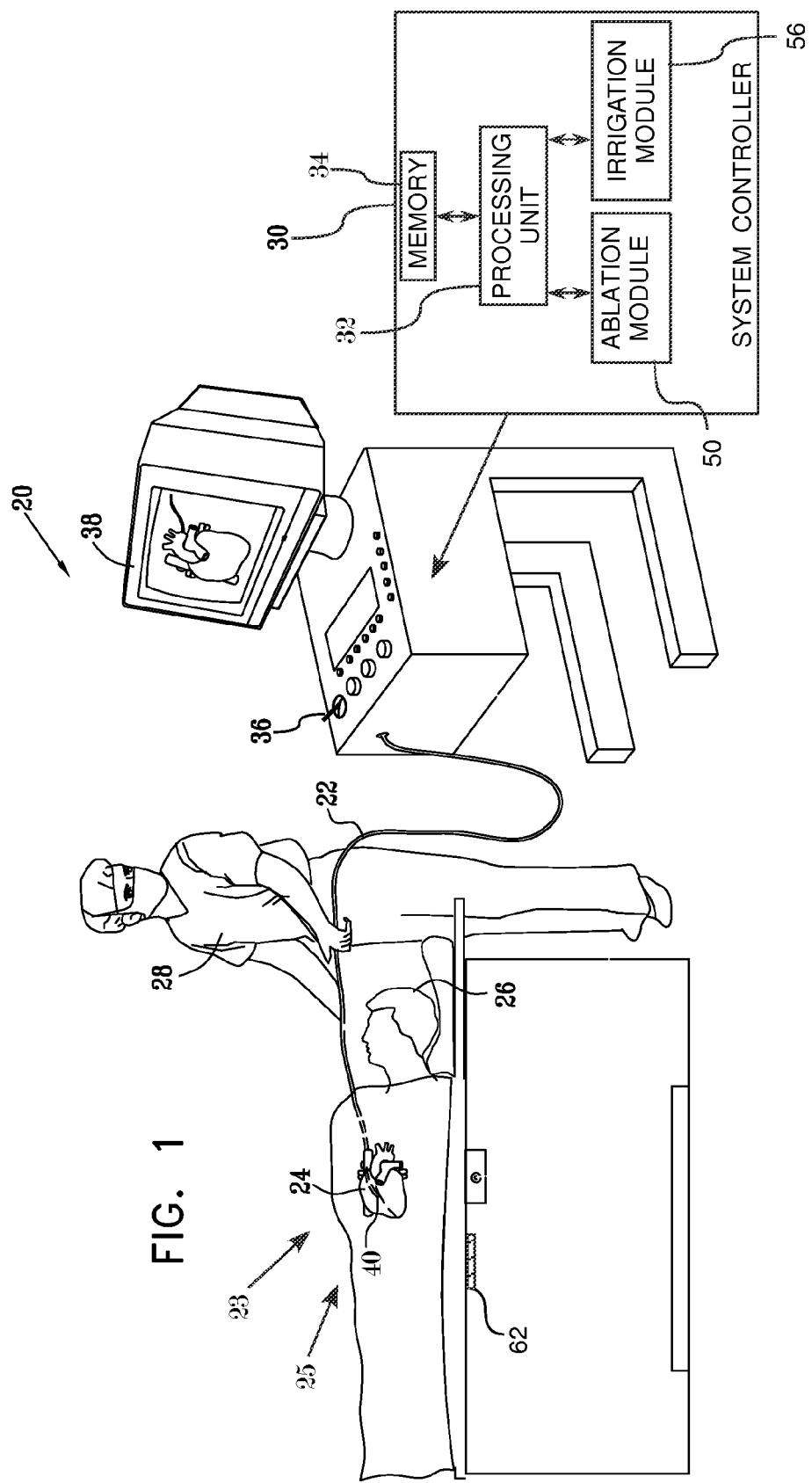
FIG. 1 is a schematic, pictorial illustration of a catheter probe ablating system, according to an embodiment of the present invention.

An embodiment of the present invention uses a mathematical model of physical parameters related to an ablation procedure. The modeled parameters represent the distal tip of a probe in proximity to body tissue during the procedure, which is performed by the probe. The ablation procedure consists of an ablation stage, in which power is applied to the body tissue at a level sufficient to ablate the tissue, and a non-ablation stage in which the power level is reduced so that no tissue ablation occurs. Typically, the period of the non-ablation stage is brief in comparison with the period of the ablation stage. During the ablation stage, a subgroup of the physical parameters is measured, generating ablative values of the subgroup. During the non-ablation stage, the subgroup of parameters is measured to generate non-ablative values of the subgroup.

The model is used to calculate ablative values of the subgroup for the ablation stage, and non-ablative values for the non-ablation stage. The measured and calculated values for the two stages are compared, so as to generate optimal values of the physical parameters.

The physical parameters that are modeled include values of power supplied by the probe, for ablating the tissue. The power may be in substantially any form, such as radio-frequency (RF), optical, or ultrasonic power. The parameters also include, but are not limited to, parameters such as a contact force of the probe on the body tissue, an irrigation rate of cooling fluid provided by the probe, impedances/conductivities of the tissue, the cooling fluid and blood surrounding the tissue, temperatures of elements in proximity to the probe, including temperatures at the distal tip, and geometrical parameters of the probe.

The model may be used to evaluate ablation of heart tissue. In one embodiment a probe having multiple electrodes is inserted into proximity with the tissue, and one or more of the electrodes transfers RF power to the tissue in the ablation procedure described above. During the procedure impedances between the electrodes and the tissue are measured, and the impedances are used to estimate a location, an orientation, and/or a contact area of the probe's distal tip with respect to the tissue. Typically, irrigation rates of the cooling fluid are altered in synchrony with the ablation procedure periods of ablation and non-ablation.

The estimate may be provided to the model which uses the estimate, as well as values of other parameters (referred to above) that are measured directly or indirectly during the ablation procedure, to produce a temperature map of the tissue being ablated.

In addition to producing the temperature map, the model may be configured to revise the estimate of the distal tip's location, orientation, and/or contact area. Typically, the process of generating and revising the estimate is performed on an iterative basis until optimal values of the location, orientation and/or contact area are attained. The model may then use the optimal values to provide a final formulation of the temperature map of the tissue.

A similar iterative process to that described above (for the probe's location, orientation, and/or contact area) may be applied for other parameters of the model.

System Description

Figure 2:
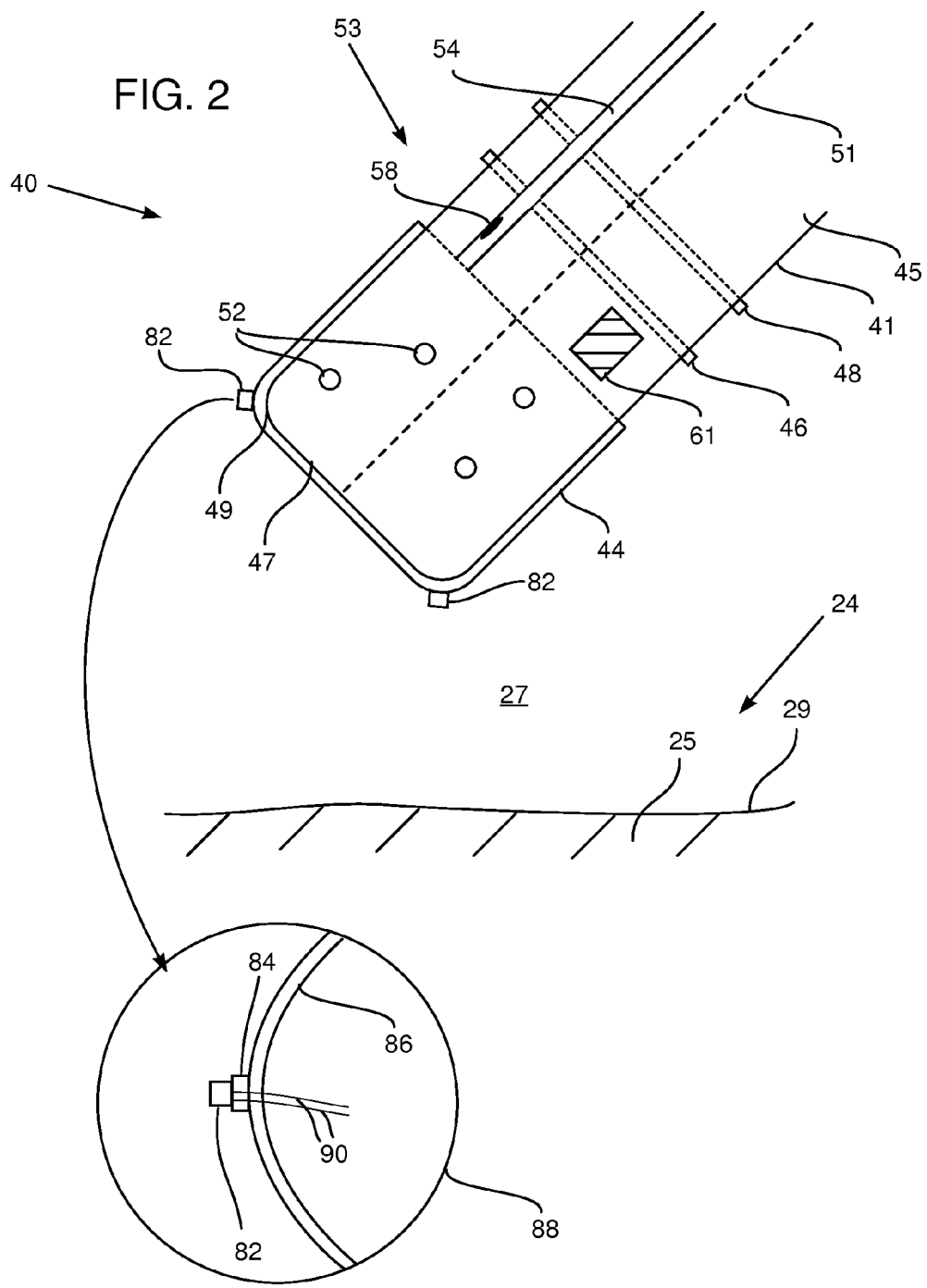
FIG. 2 is a schematic cross-section of a distal tip of a catheter probe used in the system, according to an embodiment of the present invention.

Reference is now made to FIG. 1, which is a schematic, pictorial illustration of a catheter probe ablating system 20, and to FIG. 2 which is a schematic cross-section of a distal tip of a catheter probe 22 used in the system, according to embodiments of the present invention. In system 20, probe 22 is inserted into a lumen 23, such as a chamber of a heart 24, of a subject 26. The probe is used by an operator 28 of system 20, during a procedure which includes performing ablation of body tissue 25.

The functioning of system 20 is managed by a system controller 30, comprising a processing unit 32 communicating with a memory 34, wherein is stored software for operation of system 20. Controller 30 is typically an industry-standard personal computer comprising a general-purpose computer processing unit. However, in some embodiments, at least some of the functions of the controller are performed using custom-designed hardware and software, such as an application specific integrated circuit (ASIC) or a field programmable gate array (FPGA). Controller 30 is typically operated by operator 28 using a pointing device 36 and a graphic user interface (GUI) 38, which enable the operator to set parameters of system 20. GUI 38 typically also displays results of the procedure to the operator.

The software in memory 34 may be downloaded to the controller in electronic form, over a network, for example. Alternatively or additionally, the software may be provided on non-transitory tangible media, such as optical, magnetic, or electronic storage media.

FIG. 2 illustrates in cross-section a distal tip 40 of probe 22 in proximity to tissue 25. Distal tip 40 is assumed to be immersed in fluid 27, so that tissue 25 has a surface 29 contacting the fluid. (As described below, fluid 27 typically comprises a mixture of blood and saline solution.) By way of example, distal tip 40 is assumed herein to be formed from an insulating substrate 41 in the shape of a cylinder 45 closed by a generally flat surface 47 at one end. Cylinder 45 has an axis of symmetry 51. As shown in FIG. 2, a curved section 49 joins flat surface 47 and cylinder 45. A typical diameter of cylinder 45 is 2.5 mm, and a typical radius of the curved section is 0.5 mm.

Distal tip 40 comprises a first electrode 44, a second electrode 46, and a third electrode 48, the electrodes being insulated from each other. The electrodes typically comprise thin metal layers formed over insulating substrate 41. Typically, the distal tip has other electrodes, insulated from electrodes 44, 46, and 48, which for simplicity are not shown in the diagram. Tip electrode 44 has the shape of a cup with a flat base, and is herein also referred to as the cup electrode. Cup electrode 44 typically has a thickness in a range from approximately 0.1 mm to approximately 0.2 mm. Second and third electrodes 46 and 48 are usually in the form of rings, and are also referred to herein as ring electrodes 46 and 48. In the present disclosure, electrodes 44, 46, and 48, and other electrodes of the distal tip, are also referred to herein collectively as electrodes 53.

Electrodes 44, 46, and 48 are connected to system controller 30 by wires, not shown in the figures. As described below, at least one of the electrodes is used to ablate tissue 25. An ablation module 50, under control of controller 30, is configured to be able to set and measure a level of the ablation power delivered by each of the electrodes.

Typically, during the ablation, heat is generated in the ablating electrode and in the surrounding region. In order to dissipate the heat, system 20 irrigates the region, using a number of small irrigation apertures 52 in the cup electrode. The apertures typically have diameters in an approximate range 0.1-0.2 mm. An irrigation tube 54 supplies saline solution to the apertures, and the rate of flow of the saline solution through the apertures (causing fluid 27 to be a mixture of blood and saline solution) is controlled by an irrigation module 56 in the system controller. The saline rate of flow is typically in the range of approximately 10-20 cc/minute, but may be higher or lower than this range.

A saline temperature sensor 58, typically a thermocouple, is located in tube 54, and provides a signal to module 56 allowing the module to measure a temperature $T_S$ of the saline solution input to apertures 52. While the saline solution may be provided by module 56 at room ambient temperature, e.g., in a range of approximately 19-22° C., the solution is heated during its flow in probe 22, so that temperature $T_S$ is typically in an approximate range of 26-28° C.

Typically, one or more location sensing devices 61 are incorporated in the distal tip. Devices 61 are configured to provide signals to controller 30 enabling the unit to ascertain the position and/or orientation of distal tip 40. The position and orientation are typically measured with respect to subject 26. One such location sensing device comprises the magnetic navigation CARTO system, produced by Biosense-Webster Inc, of Diamond Bar, Calif.

Alternatively or additionally, the location sensing device operates by measuring currents between electrodes 53 of the distal tip and one or more electrodes on the skin of subject 26. A skin electrode 62, which acts as a counter electrode, is assumed to be attached to subject 26. Such a method of measuring the location of distal tip 40 is disclosed in U.S. Patent Application 2010/0079158, which is incorporated herein by reference. Thus, in addition to serving as electrodes providing ablation, electrodes 53 may also be used for other functions, such as for electrophysiological sensing and/or for locating the distal tip.

As necessary, when used for other functions, controller 30 may differentiate between the currents for the different functions by frequency multiplexing. For example, ablation module 50 typically generates its ablation power at frequencies of the order of hundreds of kHz, while the position sensing frequencies may be at frequencies of the order of 1 kHz.

Typically, distal tip 40 comprises other elements, which for clarity and simplicity are not shown in FIG. 2. One such element comprises a force sensor, which is configured to measure a force exerted by tip 40 on tissue 25.

Distal tip 40 comprises one or more generally similar temperature sensors 82 (by way of example, two are shown in the diagram) which are fixedly connected, by an insulator, to the outer surface of cup electrode 44, so as to protrude from the surface. Sensors 82 have a typical diameter of approximately 0.3 mm and a length of approximately 1.5 mm. In one embodiment sensors 82 are thermistors NTC Type AB6, produced by General Electric Company of Schenectady, N.Y. In an alternative embodiment, sensors 82 comprise "Fµ" type thermistors produced by Semitec USA Corporation of Torrance, Calif. By way of example, the following description assumes there are three sensors 82 symmetrically distributed with respect to axis 51, and located on a curved section 86 of the cup electrode. Curved section 86 of the cup electrode overlays curved section 49 of the distal tip. Curved section 86 is in the shape of a partial toroid, typically a partial torus having a tube radius of approximately 0.5 mm.

A magnified section 88 of FIG. 2 illustrates one of sensors 82 in more detail. As shown in section 88, an insulator 84 separates sensor 82 from curved section 86 of the cup electrode. Insulator 84 is selected to provide good thermal and electrical insulation, and in some embodiments insulator 84 may comprise an adhesive that bonds sensor 82 to curved section 86. Wires 90 connect sensor 82 to controller 30.

By having sensors 82 protrude from the outer surface of cup electrode 44, the sensors are able to intimately contact tissue 25. Controller 30 is thus able to use signals from the sensors to provide direct temperature measurements of the tissue.

Sensors 82 typically protrude from the outer surface of the cup electrode by no more than 0.7 mm, and typically by approximately 0.5 mm.

Figure 3:
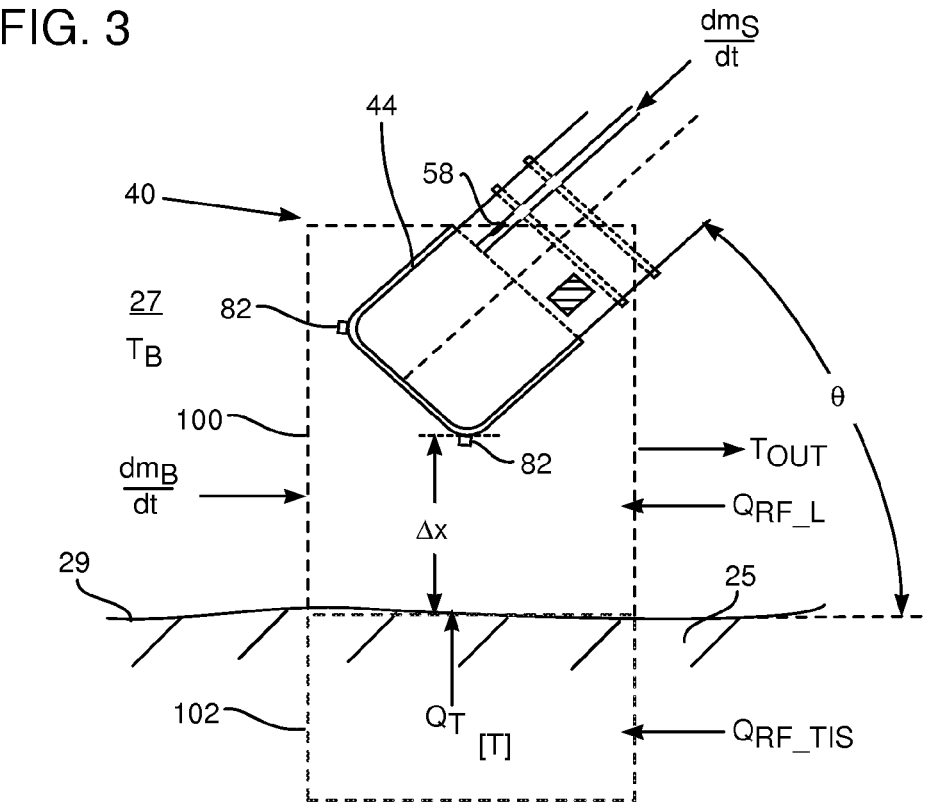
FIGS. 3 and 4 are schematic theoretical diagrams illustrating parameters used by the ablating system, according to embodiments of the present invention.
Figure 4:
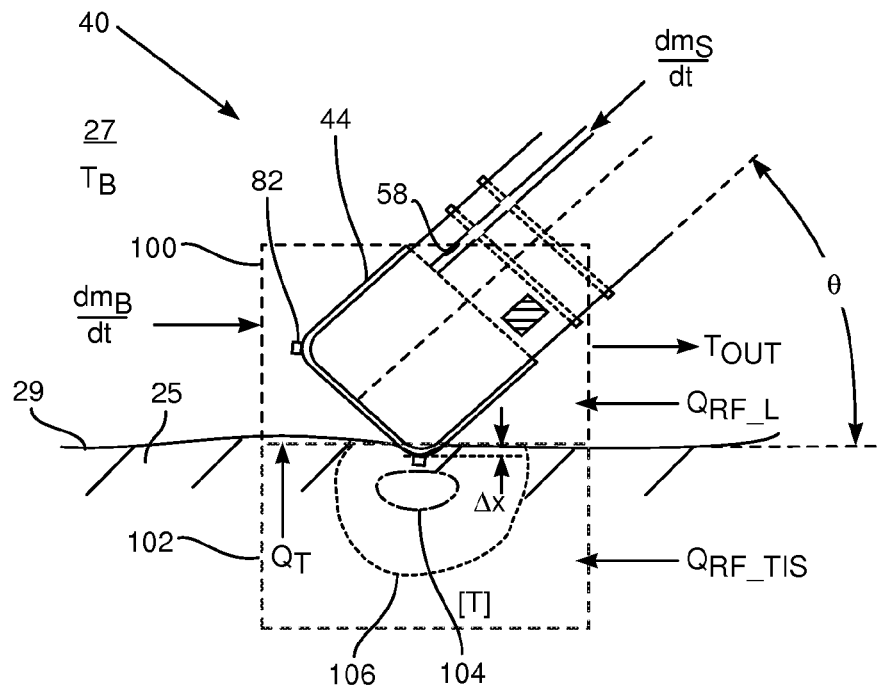

FIGS. 3 and 4 are schematic theoretical diagrams illustrating parameters used by system 20, according to an embodiment of the present invention. FIG. 3 illustrates a situation when tip 40 is above surface 29 of tissue 25, and FIG. 4 illustrates a situation when tip 40 is in contact with the tissue. System 20 estimates the temperature of tissue 25 during an ablation procedure, by controller 30 measuring and analyzing values of thermal parameters, illustrated in the figures, that are associated with the procedure.

The analysis considers the rate of energy transfer in a small volume 100 of fluid 27 surrounding cup electrode 44 and bordered by surface 29 of tissue 25. The analysis also considers the rate of energy transfer in a small volume 102 in the tissue adjacent to volume 100.

In general, an equation relating areas of distal tip 40 is:

$$A(t) = A(b) + A(c) \qquad (1)$$

where $A(t)$ is an overall area of distal tip 40 in contact with volume 100, $A(b)$ is the part of area $A(t)$ that is exposed to the fluid, and $A(c)$ is a contact area between the tip and the tissue.

In the situation illustrated in FIG. 3, $A(c)=0$, so that $A(b)=A(t)$. In the situation illustrated in FIG. 4, $A(c)>0$, so that $A(b)<A(t)$.

The power into volume 100 is assumed to be caused by electromagnetic radio-frequency (RF) ablation power $Q_{RF\_L}$ dissipated in the liquid (the blood and the saline solution) and by heat power $Q_T$ transferred into volume 100 from volume 102 of tissue 25, due to the higher temperature of the tissue compared to the temperature of blood, $T_B$. (Typically, the higher temperature of the tissue may reach approximately 90-100° C.)

The value $Q_{RF\_L}$ of the ablation power dissipated in the blood and saline solution of volume 100 is a function of the distal tip area exposed to the fluid, $A(b)$, the conductivity of the blood, $\sigma_B(T)$, and of the conductivity of the saline solution, $\sigma_S(T)$. (Both conductivities are strongly dependent on the temperature T since both have electrolytic properties. Typically the conductivities change by about 2%/° C.)

$Q_{RF\_L}$ may be written:

$$Q_{RF\_L} = Q_{RF}(\sigma_B(T), \sigma_S(T), A(b)) \qquad (2)$$

The ablation power dissipated in volume 102 (discussed in more detail below) of the tissue causes the tissue to rise in temperature above a standard body temperature assumed to be 37° C. Thus, there is an array, or map, of tissue temperatures in volume 102 of the tissue. The map of tissue temperatures may be represented by a matrix [T], where each element of the matrix is a temperature of a respective volume element in the region. The heat power transferred from volume 102 to volume 100, $Q_T$, is a function of the map of temperatures [T] and $T_B$.

Matrix [T] is illustrated schematically in FIG. 4, wherein a line 104 represents a 100° C. isotherm, and a line 106 represents a 50° C. isotherm. Regions with temperatures of 50° C. or more typically correspond to necrotic lesions.

A power, $P_{in}$, into volume 100 is given by an equation (3):

$$P_{in} = Q_{RF}(\sigma_B(T), \sigma_S(T), A(b)) + Q_T([T_T], T_B) \quad (3)$$

where $Q_T([T_T], T_B)$ is a function representing the heat power transferred into volume 100 due to differences between blood temperature $T_B$ and the temperatures of $[T_T]$, typically comprising the temperatures of the hottest part of the tissue such as those within line 104.

The power out of volume 100 is carried by the blood mass flow and by the irrigating saline solution mass flow. An expression for the power dissipated by the fluids, $P_{out}$, is:

$$P_{out} = \frac{dm_B}{dt} \cdot C_{pB} \cdot (T_{out} - T_B) + X \cdot \frac{dm_s}{dt} \cdot C_{ps} \cdot (T_{out} - T_s) \quad (4)$$

where $$\frac{dm_B}{dt}$$

is the blood mass flow, $C_{pB}$ is the specific heat capacity of the blood, $$\frac{dm_S}{dt}$$

is the saline mass flow, $C_{pS}$ is the specific heat capacity of the saline solution,
$T_S$ is the input temperature of the saline solution,
$T_B$ is the temperature of the blood entering volume 100, typically assumed to be constant at 37° C.,
$T_{out}$ is the temperature of the blood and saline solution mixture leaving volume 100, and
X is a factor depending on the amount of mixing of the saline solution and the blood in volume 100.

Typically, temperature $T_{out}$ may be determined by sensors 82. In the situation illustrated by FIG. 3, $T_{out}$ may usually be measured using all three sensors; in the situation illustrated by FIG. 4, and assuming an angle θ (defined below) is greater than approximately 45°, $T_{out}$ is typically registered by at least one of sensors 82.

Factor X in equation (4) is a function of whether the saline solution exits from irrigation apertures 52 as a turbulent or a laminar flow, since the type of flow governs the length of the saline jet exiting from each aperture. The type of flow in turn is dependent on a diameter d of the apertures and the saline mass rate of flow $$\frac{dm_S}{dt}.$$

The factor X is also dependent on the proximity of distal tip 40 to surface 29 of tissue 25 i.e., on a distance Δx between the distal tip and the surface. As illustrated, the distance Δx may be positive or negative, depending whether the distal tip is above surface 29 (FIG. 3), or below the surface (FIG. 4).

The factor X is further dependent on the directions of the flow from the apertures relative to the tissue. The directions of flow are a function of an angle θ made by distal tip 40 with tissue 25.

Thus, an energy balance equation (4) may be written:

$$P_{in} = P_{out} = \frac{dm_B}{dt} \cdot C_{pB} \cdot (T_{out} - T_B) + X \cdot \frac{dm_s}{dt} \cdot C_{ps} \cdot (T_{out} - T_s) \quad (5)$$

Considering volume 102, an ablation power $Q_{RF\_TIS}$ dissipated in the tissue may be expressed as the equation:

$$Q_{RF\_TIS} = \Sigma_V q_{TIS}(\sigma_{TIS}) \quad (6)$$

where each volume element V of volume 102 has an RF power $q_{TIS}$ dissipated in the element, according to a potential across the element and a current through the element, and where each volume element has a respective conductance $\sigma_{TIS}$.

The two ablation powers, $Q_{RF\_L}$ and $Q_{RF\_TIS}$, are supplied by ablation module 50, and are related by the equation:

$$Q_{RF} = Q_{RF\_L} + Q_{RF\_TIS} \quad (7)$$

$Q_{RF}$ is both controlled and measured by controller 30. Typically, during an ablation procedure, $Q_{RF}$ is of the order of 30 W.

As is described further below, embodiments of the present invention evaluate the expressions of equations (1)-(7). The evaluations may be used to generate values for elements of matrix [T]. In addition, the evaluations may be used to estimate values for Δx, θ, and/or A(c). In the description herein, the ordered triple (Δx, θ, A(c)) is referred to as the geometrical vector of the distal tip.

Figure 5:
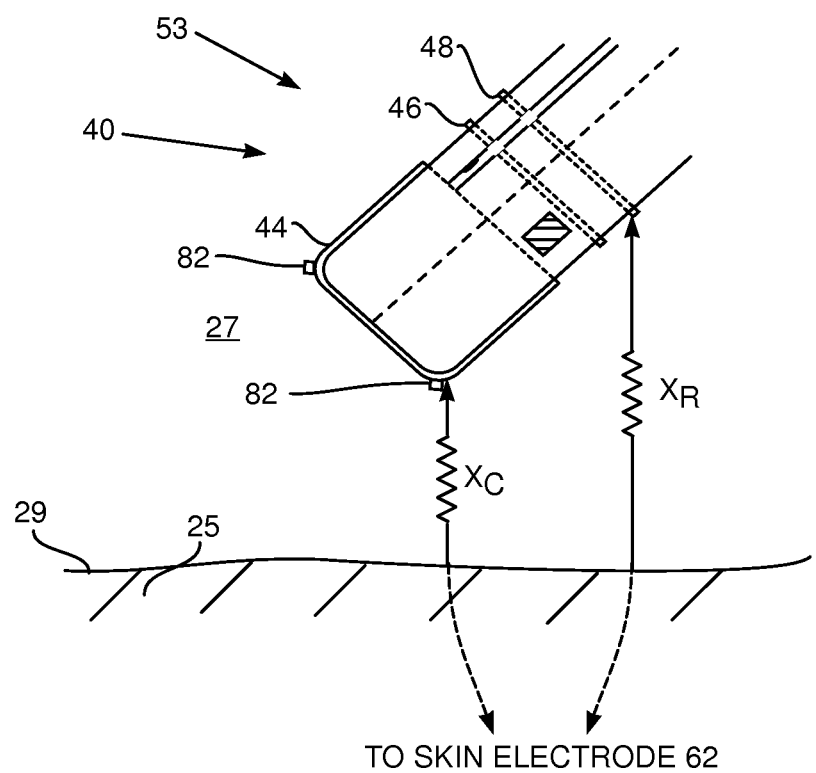
FIG. 5 is a schematic theoretical diagram illustrating a method used by the ablating system to estimate values for a geometric vector, according to an embodiment of the present invention.

FIG. 5 is a schematic theoretical diagram illustrating an alternative method used by system 20 to estimate values for Δx, θ, and/or A(c), according to an embodiment of the present invention. For simplicity, only elements of system 20 that are required for explaining the alternative method are labeled in the figure. In the alternative method, controller 30 measures an impedance $X_C$ between cup electrode 44 and skin electrode 62 (of subject 26). In addition, the controller measures an impedance $X_R$ between ring electrode 48 and the skin electrode.

The impedances $X_C$, $X_R$, are functions of the conductivity of fluid 27 in which both electrodes are immersed, and of their different effective path lengths in the fluid to surface 29. The conductivity of fluid 27 is dependent on the blood and saline conductivities, $\sigma_B(T)$, $\sigma_S(T)$. Both impedances are also functions of the conductivity of the subject tissue between surface 29 and skin electrode 62, which have substantially the same path lengths for both impedances.

As stated above, distal tip 40 typically comprises more than two electrodes, so that the explanation above may be applied for impedances between each electrode 53 and skin electrode 62.

As described below, controller 30 uses the measured impedances (after normalizing to take into account the different surface areas of the cup electrode and the one or more ring electrodes) to estimate values for Δx, θ, and/or A(c) for distal tip 40. The controller typically uses, inter alia, values of other physical parameters, such as conductivities of tissue, blood, and saline solution, to make the estimation.

Figure 6:
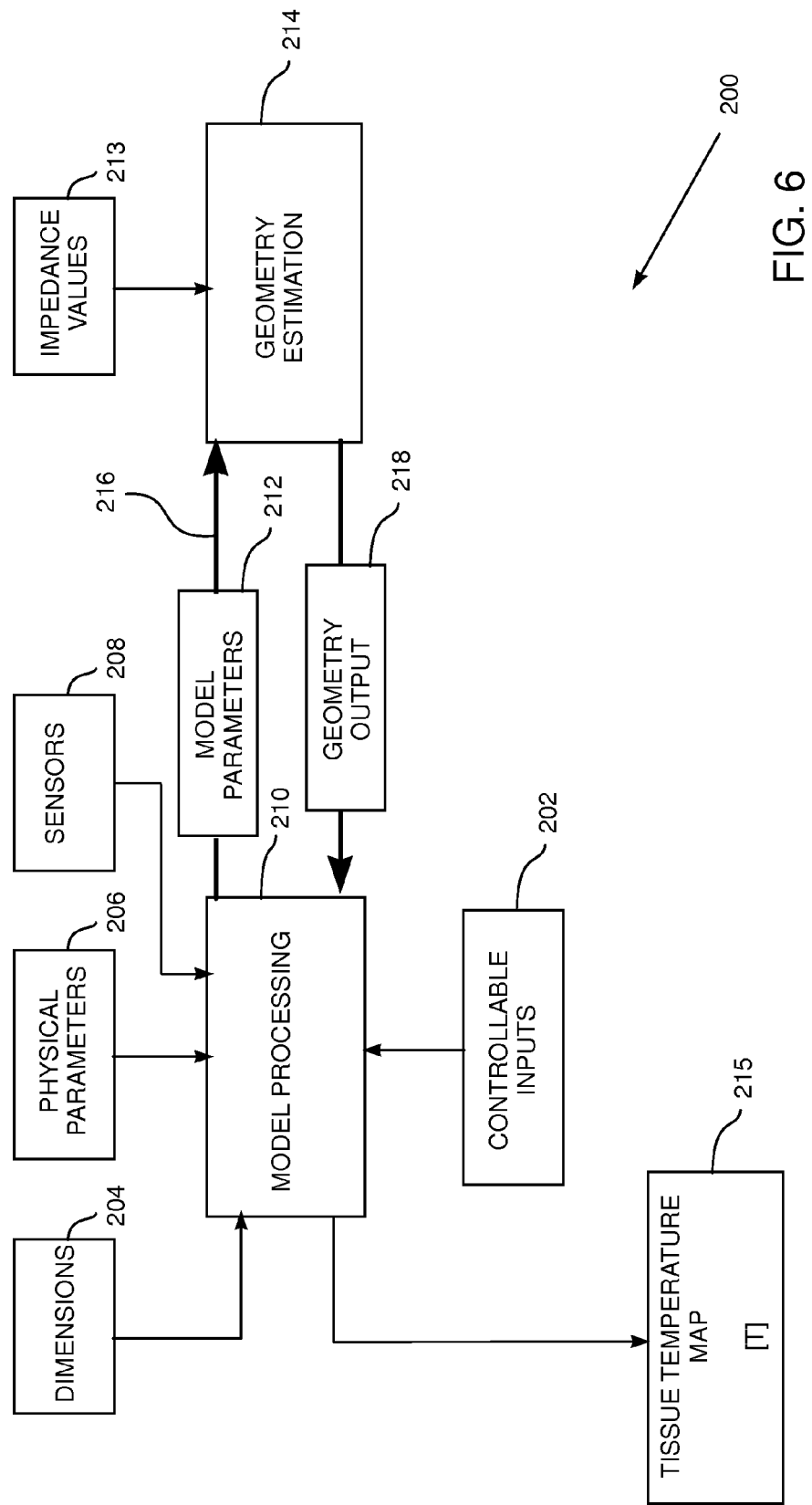
FIG. 6 is a schematic block diagram illustrating a method of analysis, according to an embodiment of the present invention.

FIG. 6 is a schematic block diagram 200 illustrating a method of analysis used by controller 30, according to an embodiment of the present invention.

A controllable inputs block 202 represents the inputs to distal tip 40 which controller 30 is configured to direct, and which the unit is able to measure. As explained above, these inputs comprise the overall ablation power generated in ablation module 50, and dissipated in volumes 100 and 102 (FIGS. 3 and 4), and the saline irrigation flow into distal tip 40.

A dimensions block 204 represents the mechanical dimensions of distal tip 40. Thus, assuming probe 22 is cylindrical, the dimensions comprise a diameter of the cylinder and a length of the distal tip that is used by the controller in its analysis.

The analysis by the controller uses values of physical parameters that are known in the art, and that may be saved in memory 34 for use by controller 30. A physical parameters block 206 represents these parameters, which comprise, for example, tissue and blood electrical conductivities, and rates of change of these conductivities with temperature. The parameters also comprise tissue thermal conductivity and its rate of change with temperature.

During an ablation procedure controller 30 is able to measure temperatures provided by saline sensor 58 and distal tip sensors 82. Typically at least one of sensors is in direct contact with tissue 25 and directly measures a tissue temperature a few tenths of a millimeter below surface 29. The controller is also able to measure the impedance presented to ablation module 50 during the procedure. In addition, the time of each of these measurements may be registered by the controller, and used to determine rates of temperature and impedance changes. A sensors block 208 represents thermal and non-thermal parameter measurements, such as those described above, which may be registered by the controller.

In a modeling process, represented by a model processing block 210, the controller incorporates the inputs of blocks 202, 204, 206, and 208 into equations (1)-(7). The modeling process typically applies finite element methods (FEMs) and computational fluid dynamics (CFD), in order to estimate values of unknown parameters of the equations, as well as to generate results of the equations. Both FEM and CFD are known in the art, and the application of these processes to analyze equations (1)-(7) will be apparent to one having ordinary skill in the art.

The controller evaluates the results of the equations, and from an analysis of the results the unit may make an estimate of thermally-dependent parameters, herein also termed thermal parameters, affecting a geometric estimation block 214, described below. The thermal parameters, represented by a model parameters block 212, typically include evaluations of the blood and saline conductivities $\sigma_B(T)$, $\sigma_S(T)$, from estimates of temperature T. From the analysis the controller may also make an estimate of the map of temperatures [T], as represented by a temperature map block 215.

In addition to the modeling process represented by block 210, controller 30 implements a geometric estimation of vector ($\Delta x$, $\theta$, A(c)), using the process described above with reference to FIG. 5. The estimation is represented by geometry estimation block 214. Block 214 receives as inputs, represented by an impedance value block 213, the impedances (measured by controller 30) between electrodes 53 and skin electrode 62. While the estimation represented by block 214 may be independently made by the controller, i.e., using only the values of block 213, the controller may apply some of the thermal parameters of block 212 in performing the estimation, as indicated by an arrow 216.

Controller 30 transfers the output of block 214, represented by a geometry output block 218, to the modeling process of block 210. Typically, as described below with reference to flowchart 300, the controller iterates between blocks 210 and 218 to generate an optimal geometric vector ($\Delta x_O$, $\theta_O$, $A(c)_O$). Thus, while an initial estimate of the vector may be substantially independent of the thermal parameters of block 212, a subsequent estimate uses the thermal parameters.

Figure 7:
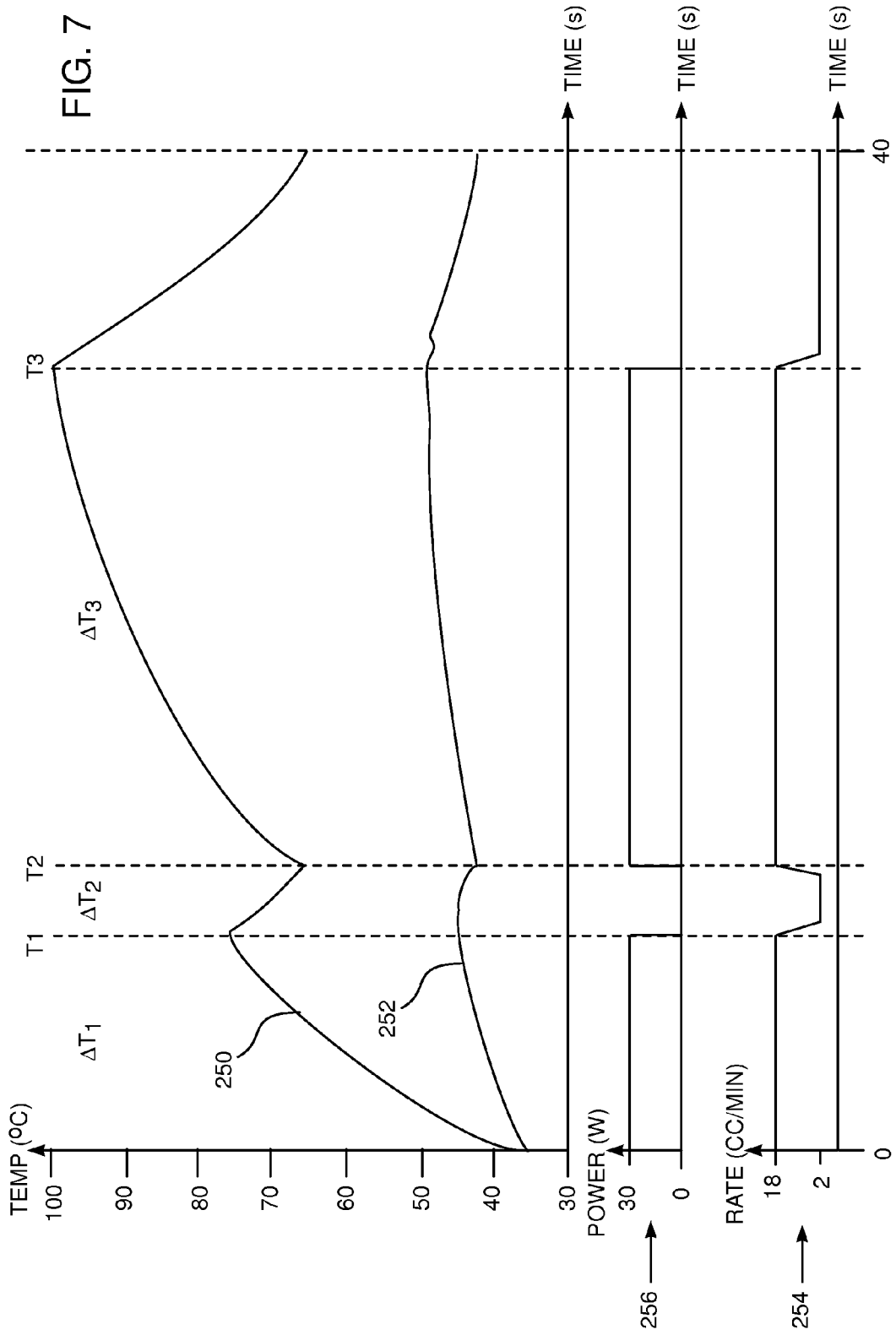
FIG. 7 illustrates schematic graphs generated by the ablating system, according to an embodiment of the present invention.

FIG. 7 illustrates schematic graphs generated by system 20, according to an embodiment of the present invention. The graphs depict simulated measurements during an intermittent ablation procedure for ablating tissue. The ablation procedure comprises ablation stages interleaved with non-ablation stages. Graphs 250 and 252 are temperature vs. time graphs, a graph 254 is of the rate of saline solution flow vs. time, and a graph 256 is of the ablation power vs. time.

During the procedure the controller applies a known ablation power, 30 W, and a known irrigation flow rate 18 cc/min, between an initial time (0s) and a time T1, for a period $\Delta T_1$. Period $\Delta T_1$ corresponds to an ablation stage of the procedure, since the power supplied during period $\Delta T_1$ is sufficient to cause necrosis of the tissue, i.e., is sufficient to ablate the tissue. At time T1, the controller switches off the ablation power and reduces the irrigation flow to 2 cc/min for a short time period $\Delta T_2$, which finishes at a time T2. In one embodiment $\Delta T_2$ is typically approximately 500 ms. During period $\Delta T_2$, corresponding to a non-ablation stage of the procedure, the tissue does not ablate. At time T2 the controller applies the ablation powers and irrigation rates used during period $\Delta T_1$, until time T3, for a period $\Delta T_3$, which is an ablation stage. From time T3, the ablation power is switched off, and the irrigation rate is reduced to the same rate as for period $\Delta T_2$. The period from T3 is a non-ablation stage.

Graph 252 shows the temperature measured by a sensor 82 of tip 40, which by way of example is assumed to be in contact with surface 29 of tissue 25. During time periods $\Delta T_1$ and $\Delta T_3$, i.e., during ablation stages wherein the tissue is being ablated, the controller is able to extract from the temperature and time measurements corresponding time constants $\tau_1$, $\tau_3$, indicative of the positive rates of change of temperature during these periods. During time period $\Delta T_2$, i.e., during non-ablation stages wherein the tissue is not being ablated, the controller evaluates a time constant $\tau_2$, indicative of the negative rate of change of temperature during period $\Delta T_2$. The controller may also evaluate a time constant $\tau_4$ for the non-ablation stage following time T3.

The controller may use the values of the time constants in the analysis performed in modeling block 210 in order to determine a corresponding temperature map [T] of the tissue being ablated. Graph 250 shows the temperature of a hot region of the tissue determined by modeling block 210.

During ablation of subject 26, the controller may perform the intermittent, "on/off," ablation procedure illustrated by graphs 254 and 256. During such an ablation procedure, the controller may measure the temperature near distal tip 40 with sensors 82, and use the temperature measurements to derive time constants for the temperature change while ablation is occurring and while it is not being performed, as exemplified above. The time constants may be used in modeling block 210 to derive a temperature map for the tissue of subject 26.

The intermittent on/off ablation procedure described above has assumed a specific value of the ablation power and a specific value of irrigation flow during the "on" stage of the procedure. Similarly, the procedure assumed another specific value of the ablation power, in this case zero, and another specific value of irrigation flow during the "off" stage of the procedure. It will be understood that these values are by way of example, and that other power and flow rate values may be implemented, and measured, by controller 30 during an on/off ablation procedure. Similarly, controller 30 may configure other values than those exemplified above for the ablation stage periods and for the non-ablation stage periods of the procedure. Using different values may allow the controller, in the analysis performed in block 210, to produce a temperature map [T} with increased accuracy.

Figure 8:
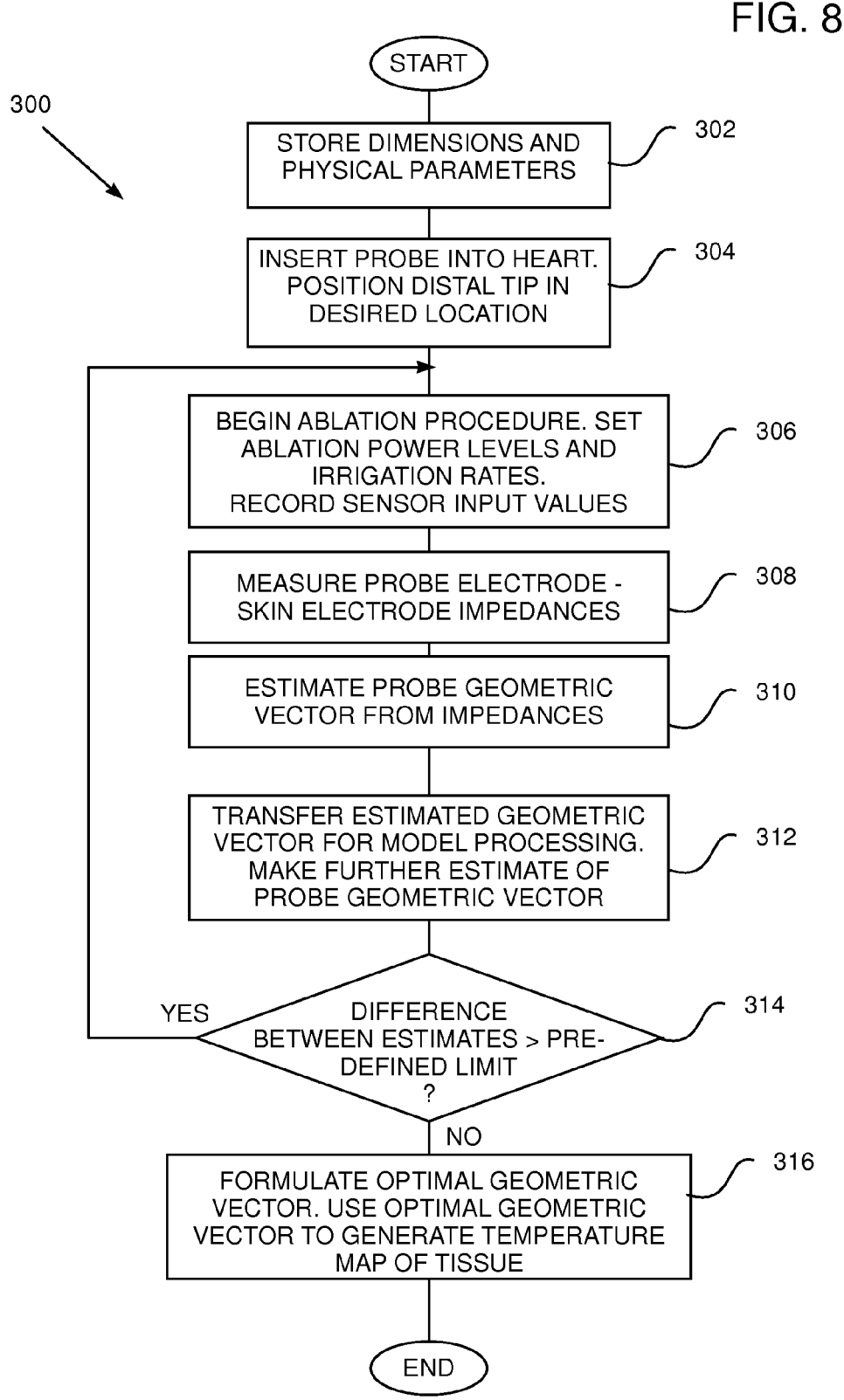
FIG. 8 is a flowchart showing steps followed by a controller of the ablating system, according to an embodiment of the present invention.

FIG. 8 is a flowchart 300 showing steps followed by controller 30, according to an embodiment of the present invention. In an initial parameter storing step 302, the unit stores values corresponding to dimensions block 204 and physical parameters block 206 (FIG. 6) in memory 34.

In an initiate procedure step 304, operator 28 inserts probe 22 into heart 24, and positions distal tip 40 in a desired location of the heart using location devices 61.

In an operational step 306, the operator begins an ablation procedure. During the procedure controller 30 adjusts and measures the ablation power provided by module 50, as well as the rate of saline irrigation provided by module 56. The procedure typically involves the intermittent on/off procedure described above with reference to FIG. 7. The parameters of controllable inputs of block 202, comprising parameters of the on and off states of the on/off procedure, may be set by operator 28. The parameters of the on and off states comprise the time periods of each state, as well as the delivered power level and saline flow rate during the states.

Alternatively or additionally, controller 30 may be configured to set the parameters of the controllable inputs of block 202. The controller may set the parameters semi-automatically, i.e. with some input from the operator, or automatically, i.e., with substantially no input from the operator. In some embodiments, the controller may set the parameters adaptively, typically in response to results derived from modeling block 210.

Also in step 306, controller 30 records the sensor input values, corresponding to sensor measurements block 208.

In an impedance measuring step 308, which is typically implemented concurrently with step 306, the controller measures impedances, described above with reference to FIG. 5, between electrodes 53 and skin electrode 62. In the case of the intermittent ablation procedure described above, the impedances may be measured during the on state and during the off state.

In a vector estimation step 310, controller 30 uses the impedances of step 308 to estimate a value for the probe geometric vector ($\Delta x$, $\theta$, A(c)). The estimation typically uses physical parameters, such as conductivities, corresponding to physical parameters block 206. In some embodiments, the controller may use the impedances to measure values of a subgroup of the elements of the geometric vector.

In a model application step 312 the values estimated in step 310 are transferred to model processing block 210, and the controller applies the processing of block 210 to make a further estimate of the geometric vector.

In a comparison step 314 the controller compares the estimates of steps 310 and 312. If the difference between the two estimates is greater than a pre-defined limit, the flowchart returns to step 306. If the difference is less than or equal to the pre-defined limit, the flowchart continues to a final step 316.

In final step 316, the controller formulates an optimal geometric vector ($\Delta x_O$, $\theta_O$, A(c)$_O$), from the vectors determined in steps 310 and 312. The controller uses the optimal geometric vector, in model processing block 210, to generate temperature map [T], corresponding to temperature map block 215. The controller typically uses a similar iterative process to that described for generating the optimal geometric vector, by comparing physical measurements of sensors such as sensors 82 with modeled values, in order to optimize temperature map [T].

While the description above assumes that the ablation power is typically RF power, it will be understood that embodiments of the present invention may use substantially any type of power for ablation, such as, but not limited to, optical or ultrasonic power.

Figure 9:
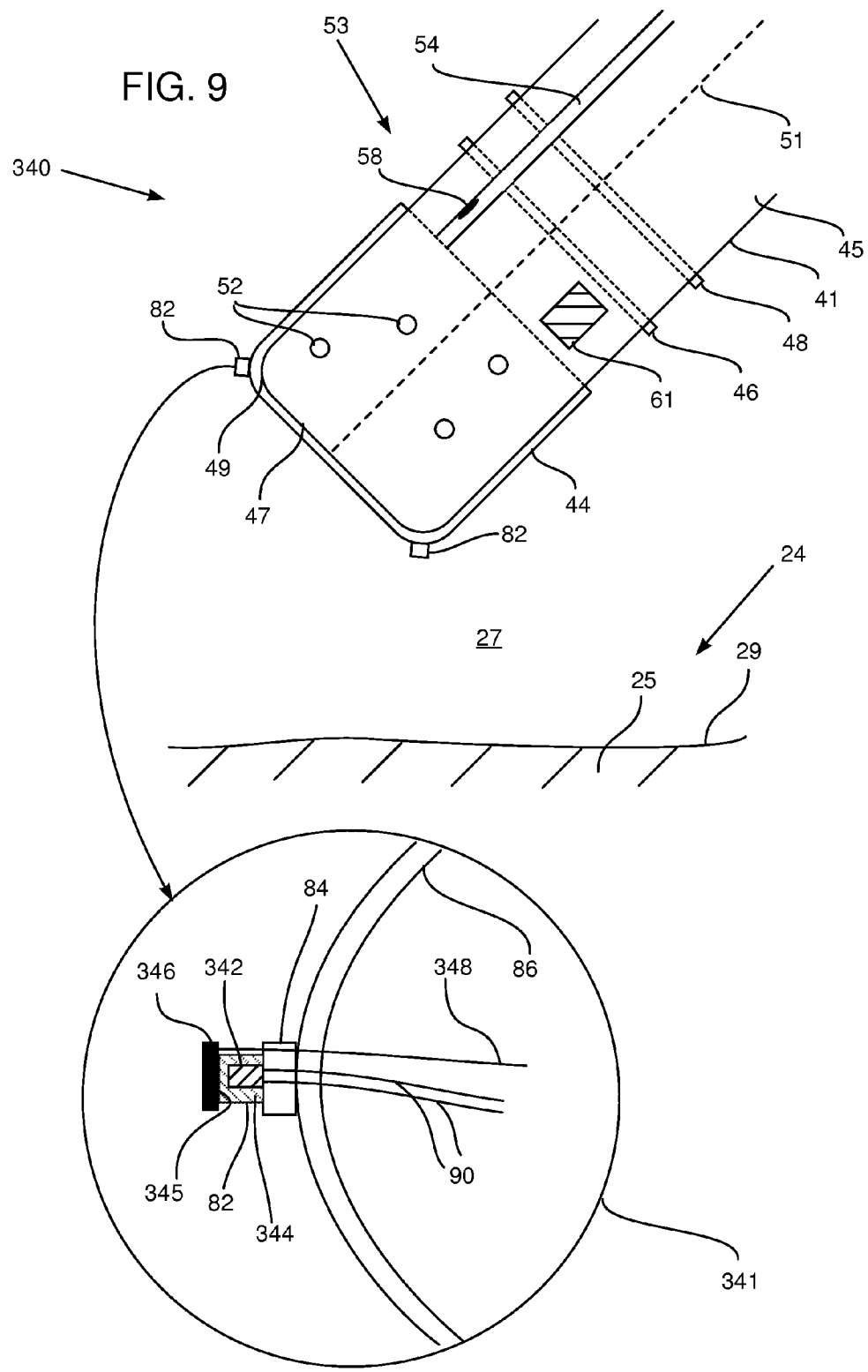
FIG. 9 is a schematic cross-section of the distal tip of the catheter probe, according to an alternative embodiment of the present invention.

FIG. 9 is a schematic cross-section of a distal tip 340 of probe 22, according to an alternative embodiment of the present invention. Apart from the differences described below, the operation of distal tip 340 is generally similar to that of distal tip 40 (FIGS. 2-8), and elements indicated by the same reference numerals in both tips 40 and 340 are generally similar in construction and in operation.

Distal tip 340 has a protruding temperature sensor (described above with reference to FIG. 2), and a magnified section 341 shows detail of sensor 82. Sensor comprises a sensing element 342, typically a semiconducting thermistor, encapsulated in an insulating package 344, usually an epoxy-filled package. Package 344 is typically both electrically and thermally insulating.

In addition, an exterior surface 345 of package 344, i.e., the surface distant from curved section 86, may be covered by a micro-electrode 346. Micro-electrode 346 is typically an inert metal such as platinum, which is formed as a coating on exterior surface 345. Alternatively, micro-electrode 346 is formed by bonding an inert metal, typically in the approximate shape of a disc, to the exterior surface using an adhesive such as adhesive 84. An insulated conductor 348, typically held in place by adhesive 84, penetrates the cup electrode and connects the micro-electrode to controller 30. Micro-electrode 346 typically has a diameter approximately equal to the diameter of sensor 82, so that its diameter is in a range of approximately 0.3 mm-approximately 0.4 mm.

A respective micro-electrode 346 is typically positioned to cover each sensor 82 as described above, and it will be understood that each micro-electrode is insulated from cup electrode 44 by insulating surface 345 and package 344. Micro-electrodes 346 have multiple functions, as described below.

Controller 30 is able to measure the impedance between each micro-electrode and skin electrode 62, and to use these measurements to estimate values of $\Delta x$ and/or $\theta$ (FIG. 5). Typically the controller uses the micro-electrode impedance measurements in addition to the impedances described above for the cup electrode and ring electrode 48, in order to improve the estimates of $\Delta x$ and/or $\theta$.

Because of the small area of the micro-electrodes (compared to the cup electrode area) the impedance measurement change when one of the micro-electrodes contacts tissue 25 is significant, as compared to the impedance change when the cup electrode contacts the tissue. At the time of contact, all of the micro-electrode is in contact with the tissue, whereas only a relatively small portion of the cup electrode makes contact. Thus, controller 30 may use the micro-electrode impedance measurement as a good indication of contact between distal tip 340 and tissue 25.

In addition to being used for impedance measurements, controller 30 may use one or more of micro-electrodes 346 for other functions, such as electrophysiological sensing and/or locating the distal tip, as described above for electrodes 53.

Figure 10:
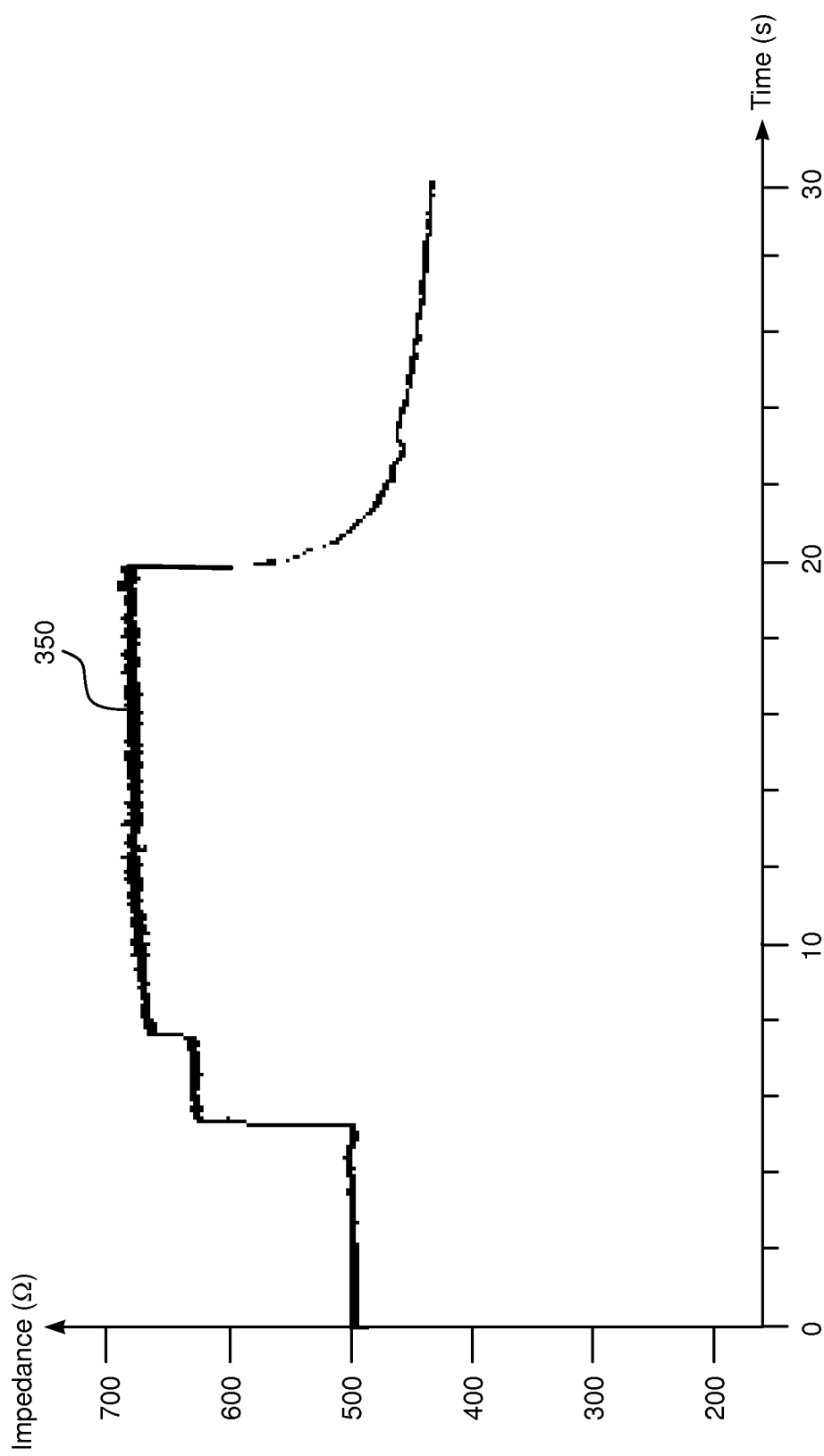
FIG. 10 is a schematic graph of impedance vs. time, according to an embodiment of the present invention.

FIG. 10 is a schematic graph 350 of impedance vs. time, according to an embodiment of the present invention. Graph 350 illustrates uses of micro-electrode 346 described above, and plots the impedance between the micro-electrode and electrode 62, during an ablation procedure wherein the micro-electrode is in the vicinity of tissue 25. During the first 5 s of the procedure, the micro-electrode does not touch the tissue, and the impedance is approximately 500Ω. At 5 s the micro-electrode contacts surface 29 of the tissue, and the impedance rises sharply to approximately 640Ω. The micro-electrode remains in contact with the tissue for 2 s, until 7 s, as shown by the constant impedance of approximately 640 Ω.

At 7 s micro-electrode 346 penetrates approximately 0.7 mm into tissue 25, causing a further sharp rise in the impedance to approximately 680Ω. (The rise is assumed to be caused by the micro-electrode being more completely surrounded by tissue 25, compared to the initial contact state.) The inventors have found that the change in impedance, illustrated by the increase from 640Ω to 680Ω, is a good indication of the depth of penetration of the portion of the tip comprising the micro-electrode into the tissue.

The impedance remains constant at 680Ω until 20 s, at which time ablation is started. The impedance decay from 20 s on is believed to be due to the temperature rise of the tissue, which in turn increases the conductivity of the tissue.

Figure 11:
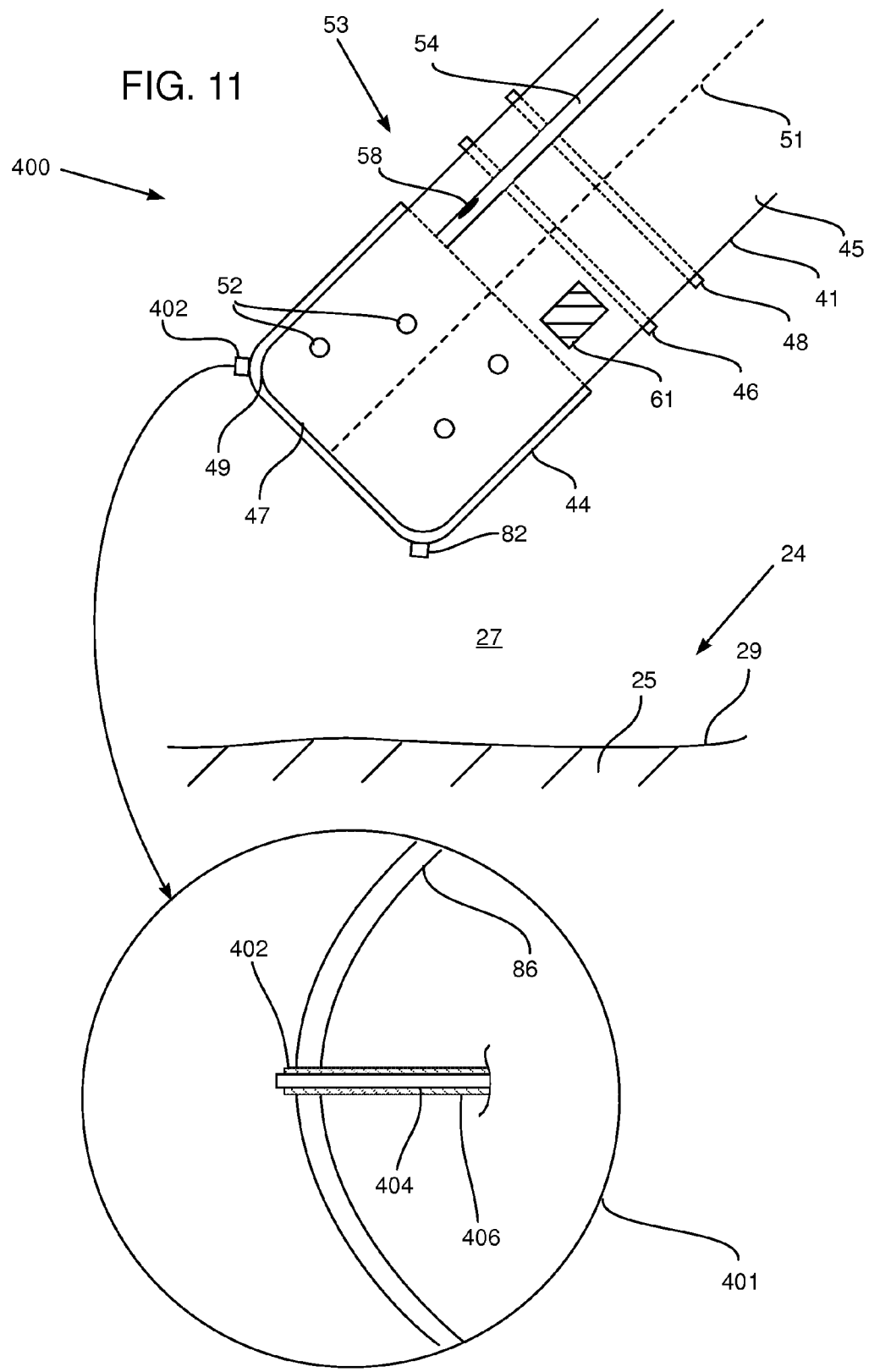
FIG. 11 is a schematic cross-section of an alternative distal tip of the catheter probe, according to an embodiment of the present invention.
Figure 12:
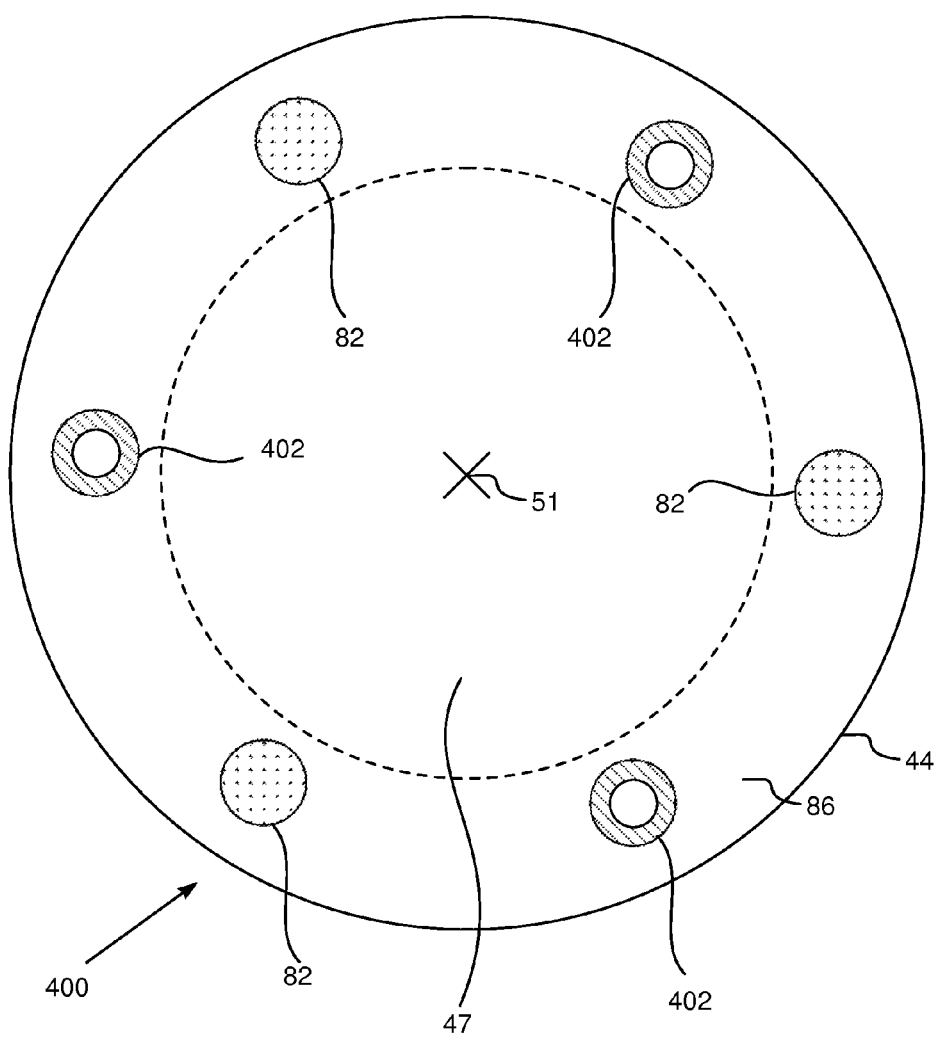
FIG. 12 is a schematic external view of the alternative distal tip of the catheter probe.

FIG. 11 is a schematic cross-section of a distal tip 400 of probe 22, and FIG. 12 is a schematic external view of tip 400, according to an alternative embodiment of the present invention. FIG. 12 is a view of the distal tip along axis of symmetry 51. Apart from the differences described below, the construction of distal tip 400 is generally similar to that of distal tip 40 (FIG. 2), and elements indicated by the same reference numerals in both tips 40 and 400 are generally similar in operation and construction.

In addition to one or more temperature sensors 82, tip 400 comprises one or more substantially similar micro-electrode assemblies 402. A magnified section 401 shows detail of assembly 402. In the following description, by way of example tip 400 is assumed to comprise three assemblies 402 and three sensors 82 distributed symmetrically on curved section 86 of cup electrode 44, around axis 51. Typically, each sensor 82 is covered by a respective micro-electrode 346, as described above with reference to FIG. 9.

Each assembly 402 is able to perform substantially the same functions as micro-electrode 346. Assembly 402 comprises an inert conducting wire 404, for example a platinum wire, which is connected to controller 30. Wire 404 is encased in an insulating tube 406, typically formed from a polyamide, the tube insulating the wire from cup electrode 44. Typically, the wire of the assembly is configured to protrude slightly from tube 406, as illustrated in the figure, so that the tip of the wire acts as an electrode insulated from cup electrode 44.

Using methods substantially as described above for tips 40 and 340, controller 30 is able to use the data from sensors 82, micro-electrodes 346, and assemblies 402 to determine:
a temperature map of tissue 25,
a location and an orientation of distal tip 400;
contact of tip 400 with tissue 25; and
a depth of penetration of tip 400 into tissue 25.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
    a probe having a longitudinal axis, configured to be inserted into a body cavity;
    an electrode connected to the probe, the electrode having a cup shape with a flat base with an outer surface and an inner surface;
    a temperature sensor fixedly connected to and protruding from the outer surface of the electrode, the temperature sensor being thermally and electrically isolated from the electrode and configured to measure a temperature of the body cavity; and
    a micro-electrode assembly, protruding from the outer surface of the electrode, the micro-electrode assembly being insulated from the electrode, wherein the temperature sensor and micro-electrode are distributed in spaced apart relation about the longitudinal axis.

2. The apparatus according to claim 1, wherein the temperature sensor protrudes from the outer surface of the electrode by no more than 0.7 mm.

3. The apparatus according to claim 1, wherein the electrode comprises a curved surface in the shape of a partial toroid, and wherein the temperature sensor protrudes from the curved surface.

4. The apparatus according to claim 1, and comprising at least one further temperature sensor protruding from the outer surface of the electrode and configured to measure a further temperature of the body cavity.

5. The apparatus according to claim 1, and comprising an insulator which connects the temperature sensor to the outer surface.

6. The apparatus according to claim 1, and comprising a further electrode positioned on an exterior surface of the temperature sensor, wherein the exterior surface insulates the further electrode from the electrode.

7. The apparatus according to claim 6, wherein contact between a distal tip of the probe and tissue of the body cavity is determined in response to an impedance of the further electrode.

8. The apparatus according to claim 6, wherein a distance between a distal tip of the probe and tissue of the body cavity is measured in response to an impedance of the further electrode.

9. The apparatus according to claim 6, wherein an angle between a distal tip of the probe and tissue of the body cavity is measured in response to an impedance of the further electrode.

10. The apparatus according to claim 6, wherein a depth of penetration of a distal tip of the probe into the tissue is determined in response to an impedance of the further electrode.

11. The apparatus according to claim 6, wherein at least one of a location and an orientation of a distal tip of the probe is determined in response to an impedance of the further electrode.

12. The apparatus according to claim 6, wherein a temperature map of tissue of the body cavity is determined in response to an impedance of the further electrode.

13. The apparatus according to claim 1, wherein the electrode comprises a first electrode, the apparatus further comprising a second electrode protruding from the outer surface of the first electrode and insulated from the first electrode.

14. A method, comprising:
    configuring a probe to be inserted into a body cavity;
    connecting an electrode having a cup shape with a flat base with and an outer surface and an inner surface to the probe;
    fixedly connecting a temperature sensor to the outer surface of the electrode and configuring the temperature sensor to be electrically and thermally insulated from the electrode, to protrude from the outer surface of the electrode and to measure a temperature of the body cavity; and configuring a micro-electrode assembly to protrude from the outer surface of the electrode, the micro-electrode assembly being insulated from the electrode, wherein the temperature sensor and micro-electrode are distributed in spaced apart relation about the longitudinal axis.

15. The method according to claim 14, wherein the temperature sensor protrudes from the outer surface of the electrode by no more than 0.7 mm.

16. The method according to claim 14, wherein the electrode comprises a curved surface in the shape of a partial toroid, and wherein the temperature sensor protrudes from the curved surface.

17. The method according to claim 14, and comprising configuring at least one further temperature sensor to protrude from the outer surface of the electrode and to measure a further temperature of the body cavity.

18. The method according to claim 14, and comprising connecting the temperature sensor to the outer surface by an insulator.

19. The method according to claim 14, and comprising positioning a further electrode on an exterior surface of the temperature sensor, wherein the exterior surface insulates the further electrode from the electrode.

20. The method according to claim 19, and comprising determining contact between a distal tip of the probe and tissue of the body cavity in response to an impedance of the further electrode.

21. The method according to claim 19, and comprising measuring a distance between a distal tip of the probe and tissue of the body cavity in response to an impedance of the further electrode.

22. The method according to claim 19, and comprising measuring an angle between a distal tip of the probe and tissue of the body cavity in response to an impedance of the further electrode.

23. The method according to claim 19, wherein a depth of penetration of a distal tip of the probe into the tissue is determined in response to an impedance of the further electrode.

24. The method according to claim 19, wherein at least one of a location and an orientation of a distal tip of the probe is determined in response to an impedance of the further electrode.

25. The method according to claim 19, wherein a temperature map of tissue of the body cavity is determined in response to an impedance of the further electrode.

26. The method according to claim 14, wherein the electrode comprises a first electrode, the method further comprising configuring a second electrode to protrude from the outer surface of the first electrode and to be insulated from the first electrode.

27. An apparatus, comprising:
a probe having a longitudinal axis with a proximal end and a distal end terminating in a distal tip, configured to be inserted into a body cavity;
an electrode having a cup shape with a flat base, and an outer surface and an inner surface connected to the distal tip of the probe;
a plurality of temperature sensors fixedly connected to and protruding from the outer surface of the electrode, each temperature sensor being thermally and electrically isolated from the electrode and configured to measure a temperature of the body cavity; and
a plurality of micro-electrode assemblies protruding from the outer surface of the electrode, the micro-electrode assemblies being insulated from the electrode and configured to measure impedance, wherein the temperature sensors and micro-electrodes are distributed in symmetrically spaced apart relation about the longitudinal axis.

28. An apparatus, comprising:
a probe having a longitudinal axis, configured to be inserted into a body cavity;
an electrode having an outer surface and an inner surface connected to the probe;
a temperature sensor fixedly connected to and protruding from the outer surface of the electrode, the temperature sensor being thermally and electrically isolated from the electrode and configured to measure a temperature of the body cavity; and
a micro-electrode assembly fixedly connected to and protruding from the outer surface of the electrode, the micro-electrode assembly comprising an inert conducting wire encased in an insulating tube, the tube insulating the wire from the electrode, wherein the wire protrudes from the tube so that the tip of the wire acts as an electrode.

* * * * *